(12) United States Patent
Chainer et al.

(10) Patent No.: US 8,589,102 B2
(45) Date of Patent: Nov. 19, 2013

(54) USING IN SITU CAPACITANCE MEASUREMENTS TO MONITOR THE STABILITY OF INTERFACE MATERIALS IN COMPLEX PCB ASSEMBLIES AND OTHER STRUCTURES

(75) Inventors: Timothy J. Chainer, Putnam Valley, NY (US); Michael A. Gaynes, Vestal, NY (US); Edward J. Yarmchuk, Creedmoor, NC (US)

(73) Assignee: International Business Machines Corporation, Armonk, NY (US)

( * ) Notice: Subject to any disclaimer, the term of this patent is extended or adjusted under 35 U.S.C. 154(b) by 343 days.

(21) Appl. No.: 13/010,854

(22) Filed: Jan. 21, 2011

(65) Prior Publication Data
US 2012/0053874 A1  Mar. 1, 2012

Related U.S. Application Data

(60) Provisional application No. 61/377,281, filed on Aug. 26, 2010.

(51) Int. Cl.
*G01N 27/22* (2006.01)

(52) U.S. Cl.
USPC ............................................................ 702/65

(58) Field of Classification Search
USPC ............................................................ 702/65
See application file for complete search history.

(56) References Cited

U.S. PATENT DOCUMENTS

| | | | |
|---|---|---|---|
| 5,825,087 A | 10/1998 | Iruvanti | |
| 7,764,069 B2 * | 7/2010 | Gaynes et al. | 324/662 |
| 8,026,730 B2 * | 9/2011 | Gaynes et al. | 324/662 |
| 2008/0265867 A1 * | 10/2008 | Gaynes et al. | 324/71.5 |

OTHER PUBLICATIONS

Agilent 4263B LCR Meter Operation Manual, 330 pages, 2009 Agilent Technologies.*
Joe Doman. et al "Evaluation of Thermal Interface Material Performance in a Cyclic Strain Environment" presented at 2010 SMTAI.
Michael Gaynes. et al "Using insitu Capacitance Measurements to Monitor the Stability of Thermal Interface Materials in Complex PCB Assemblies" presented at IMAPS 2010.
Anon., Thermal interface material, retrieved from Wikipedia, http://en.wikipedia.org/wiki/Thermal_interface_material, Aug. 17, 2010.

* cited by examiner

*Primary Examiner* — Tung S Lau
(74) *Attorney, Agent, or Firm* — Daniel P. Morris; Otterstedt, Ellenbogen & Kammer, LLP

(57) ABSTRACT

An electric potential is applied to first and second electrodes on opposite sides of a gap between an electronic component and a heat spreader. At least one of a thermal interface material in the gap, the electronic component and the heat spreader is subjected to a changing physical condition. The electrical capacitance between the electrodes is monitored during the changing physical condition. Such a method can be practiced using an array of components sharing a common heat spreader. An assembly for testing thermal interfaces includes a printed circuit board, a plurality of electronic components mounted to and operatively associated with the printed circuit board, a heat spreader positioned for absorbing heat generated by the electronic components, a first electrode associated with the heat spreader, a plurality of second electrodes associated, respectively, with the electronic component, and a device for monitoring electrical capacitances between the first and second electrodes. The technique may be employed for monitoring physical changes in electronic devices and other structures having interfaces between components.

15 Claims, 17 Drawing Sheets

USING IN SITU CAPACITANCE MEASUREMENTS TO MONITOR THE STABILITY OF INTERFACE MATERIALS IN COMPLEX PCB ASSEMBLIES AND OTHER STRUCTURES

CROSS-REFERENCE TO RELATED APPLICATIONS

This patent application claims the benefit of U.S. Provisional Patent Application Ser. No. 61/377,281 filed on Aug. 26, 2010, and entitled "Using in Situ Capacitance Measurements to Monitor the Stability of interface Materials in Complex PCB Assemblies." The disclosure of the aforementioned Provisional Patent Application Ser. No. 61/377,281 is expressly incorporated herein by reference in its entirety for all purposes.

FIELD OF THE INVENTION

The present invention relates to the electronic, thermal, and mechanical arts, and, more particularly, to thermal control and monitoring of electronic modules and other structures.

BACKGROUND OF THE INVENTION

Thermal interface materials ("TIM") are employed to fill the gaps between thermal transfer surfaces. For example, such materials can fill the gaps between electronic components and heat sinks. They allow the conduction of heat from the components to the heat sinks. TIM can be made from various materials. TIM properties can be different depending on their composition.

SUMMARY OF THE INVENTION

Principles of the invention provide techniques for using in situ capacitance measurements to monitor the stability of materials exhibiting dielectric properties, such as certain thermal interface materials, in structures such as complex PCB (printed circuit board) assemblies. In one aspect, an exemplary method includes the steps of applying an electric potential to first and second electrodes on opposite sides of a gap between an electronic component and a heat spreader, subjecting at least one of a thermal interface material in the gap, the electronic component and the heat spreader to a changing physical condition, and monitoring the electrical capacitance between the electrodes during the changing physical condition. Such a method can be practiced using an array of components sharing a common heat spreader.

In another aspect, an exemplary assembly for testing thermal interfaces includes a printed circuit board; a plurality of electronic components mounted to and operatively associated with the printed circuit board; a heat spreader positioned for absorbing heat generated by the electronic components; a first electrode associated with the heat spreader; a plurality of second electrodes associated, respectively, with the electronic components; and a device for monitoring electrical capacitances between the first and second electrodes.

In a further aspect, an exemplary method of constructing an assembly capable of being monitored for physical changes includes the steps of providing a plurality of components, providing interface material, providing a plurality of electrode plates, providing a plurality of conductors, and assembling the components, the interface material, the electrode plates and the conductors to form an integral structure wherein a plurality of interfaces are provided between the components, the electrode plates are positioned within the interfaces, the interface material is positioned between the electrode plates, and the conductors are electrically connected to the electrode plates and are externally accessible on the integral structure. The method may further include providing an apparatus for measuring electrical capacitance and connecting the apparatus to the conductors.

As used herein, "facilitating" an action includes: performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer product including a tangible computer readable recordable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s), or (iii) a combination of hardware and software modules; any of (i)-(iii) implement the specific techniques set forth herein, and the software modules are stored in a tangible computer-readable recordable storage medium (or multiple such media).

Techniques of the present invention can provide substantial beneficial technical effects. For example, one or more embodiments may provide one or more of the following advantages:

- The air gap in which the thermal interface material or other material will reside can be accurately measured before depositing the material, which allows knowing the ultimate bond line for the material. These air gap measurements can also be compared to specification targets with tolerances for the material to ensure, for example, that a heat spreader and electronic assembly meet their respective design targets for dimensions such as x, y and z location;
- The bond line can be measured in real time during the attachment of one element to another, for example the attachment of a heat spreader to an electronic assembly. Processes to attach the heat spreader can accordingly be developed and optimized to ensure that the target TIM gap is reached;
- Average thermal performance can be predicted for a complex electronic assembly before designing and building special thermal functional test hardware. This capability allows detection of time zero design deficiencies as well as environmental stress test driven degradation that would result in unreliable field performance;
- Gap motion can be measured as a function of temperature, which allows the design of thermal mechanical experiments on model samples to evaluate mechanical stability of TIMs and the impact of surface treatments and mechanical constraints on TIM stability.

These and other features and advantages of the present invention will become apparent from the following detailed description of illustrative embodiments thereof, which is to be read in connection with the accompanying drawings.

DETAILED DESERT PREFERRED EMBODIMENTS

Figure 1:
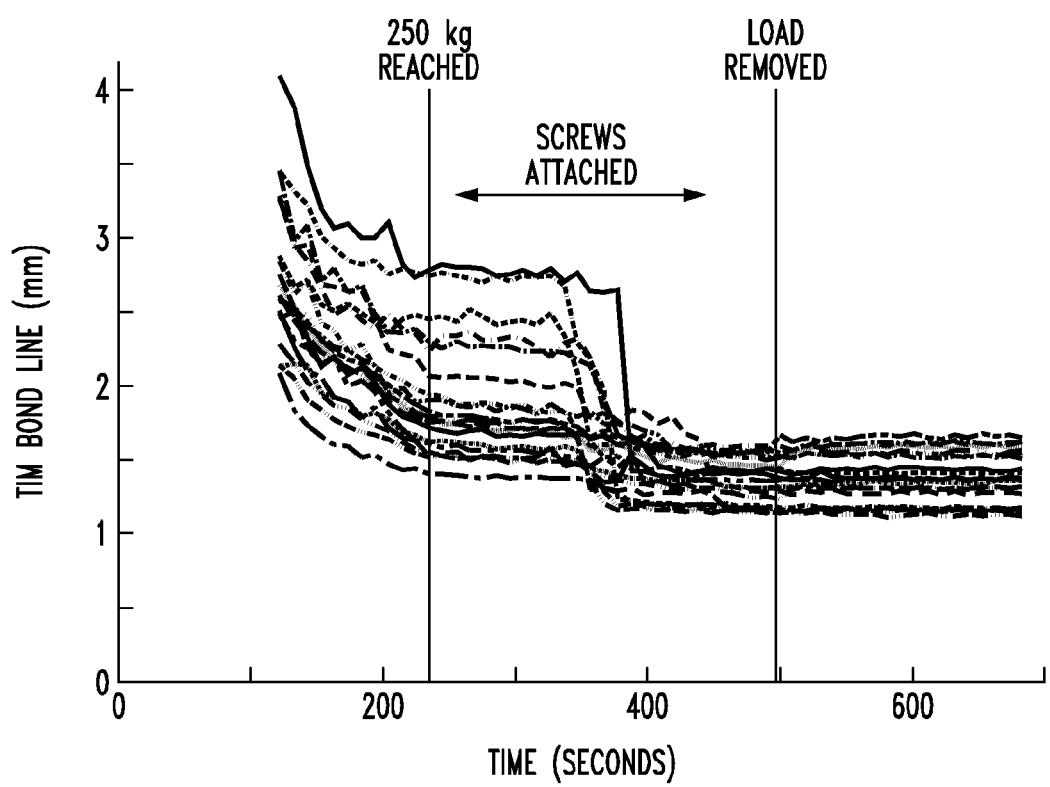
FIG. 1 shows a graph of a TIM bond line response to load, time and fastening of a heat spreader to a printed circuit board.

Aspects of the invention pertain to monitoring thermal interface materials used in conjunction with electronic components such as modules and/or other electronic devices. As noted above, thermal interface materials ("TIM") are employed to fill the gaps between thermal transfer surfaces. Materials used to fill the gaps between electronic components and heat sinks often include polymeric materials tilled with thermally conductive tillers. The polymeric materials may include greases, gels, waxes, elastomers, and rigid thermosets and thermoplastics. Thermally conductive fillers often include silica, alumina, boron nitride, aluminum nitride, aluminum, or zinc oxide. Pre-cured, room temperature curable, thermal or light curable, or non-curing TIMs are available. The methods described herein are applicable to materials having a measurable dielectric constant. Accordingly, electrically conductive fillers could be present in the materials as long as the materials continue to support an electrostatic field (for example, under circumstances where filler content is below the percolation threshold where isotropic electrical conductivity is not possible). Electrically conductive fillers found in some TIMs include silver, gold, copper and nickel. TIMs allow the conduction of heat from the components to the heat sinks. TIM properties can be different depending on their composition. An embodiment of the invention provides a thermal solution for an array of electronic components, namely voltage transformer modules. The modules are arranged to be cooled by a large area, common aluminum heat spreader for a high end server. An in-situ, capacitive bond line thermal measurement technique is used to measure the capacitance of a non-electrically conducting thermal interface material (TIM) between one or more of the electronic modules and the heat spreader to quantify the TIM bond line effective thickness during assembly, testing and operation. The thermal resistance of the TIM has the same geometric dependence as the inverse of capacitance. Accordingly, the capacitive technique also allows the monitoring of the thermal performance of the interface. It will be appreciated that the disclosed technique has possible application to a wide variety of electronic components that are thermally interfaced to heat sinks by TIM, whether employed in servers or other electronic apparatus.

The capacitive technique was applied to measure the bond line in real time during the assembly of the heat spreader to an array of thirty-seven modules mounted on a printed circuit board (PCB). The results showed that the target bond lines were not achieved by application of a constant force alone on the heat spreader and guided an improved assembly process.

The mechanical motion of the TIM was monitored in-situ during several hundred thermal cycles and found to fluctuate systematically from the hot to cold portions of the thermal cycle, either compressing or stretching the TIM, respectively. The capacitive bond line trend showed thermal interface degradation vs. cycle count for several modules, which was confirmed by disassembly and visual inspection. Areas of depleted TIM ranged as high as 25% of the component area.

Several design and material changes were shown to improve the TIM stability. Such improvements were detected through performance of the capacitance technique, as described further below, and confirmed by visual inspection. Power cycling tests were run in parallel to thermal cycle tests to help relate the results to field performance. The capacitance technique enabled the development and verification of a thermal solution for a complex mechanical system very early in the development cycle.

Heat sinks have been individually attached to a variety of components on complex printed board assemblies. As packaging integration increases, more design forethought is required to ensure efficient and effective removal of heat from high power electronic modules. More control over air flow is possible when a common heat spreader is interfaced to the various high heat generating modules. Air flow can be directed down channels that are integrated into the heat spreader. There are certain challenges when using a common heat spreader. A large area heat spreader that is thermally interfaced to many components will require greater force to reach the target bond line of the thermal interface material (TIM.) The several components, which could be the same design or a variety of designs, may have different heights above the printed circuit board (PCB.) The TIM should easily accommodate tolerances in height which typically could be +/−0.5 mm for a nominal gap of 1.5 mm. Similarly, it should be easy to separate the heat spreader afterwards in case one or more components fail electrical testing and require replacement. During the removal of the heat spreader, it is preferable that the separation forces are low enough to prevent electrically good components from being damaged. Finally, TIM structural integrity is typically required across all components to provide a reliable thermal path for heat transfer during the life cycle of the product.

Figure 19A:
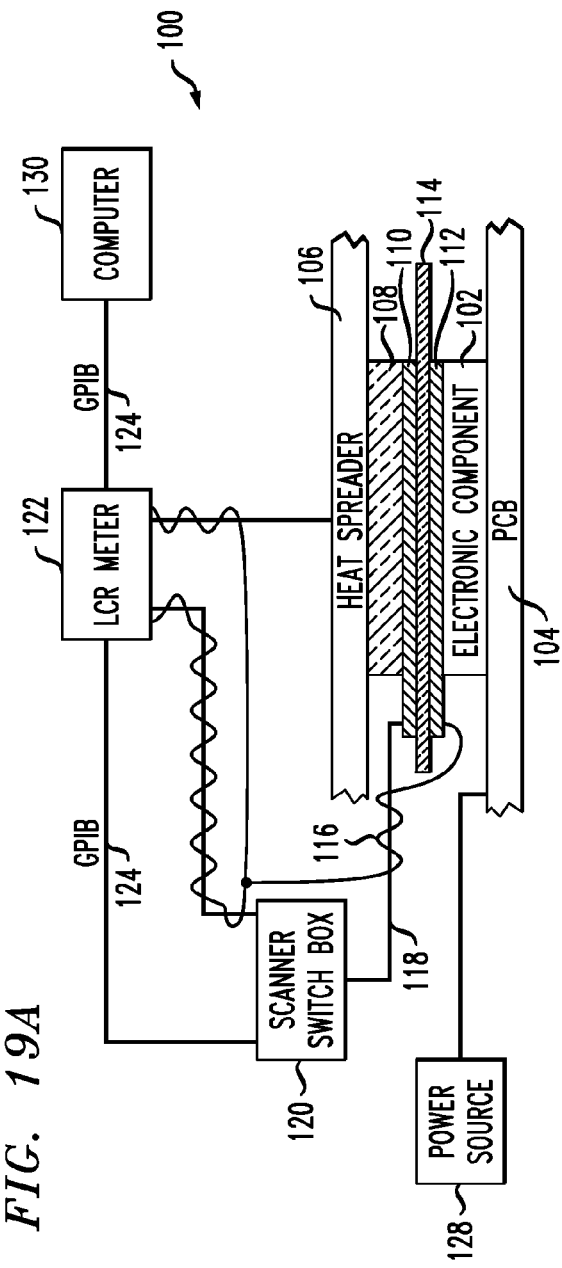
FIG. 19A is a schematic diagram showing an assembly for determining the capacitance of TIM in a gap between an electronic component and a heat spreader.

Voltage transformer modules 102 intended for use in a high end server are employed in experimental performance of the capacitance technique disclosed herein. FIG. 19A shows an assembly 100 for performing the technique. As discussed below, shielding of the wires and electronic components as shown in the figure is preferred though not required for performing the technique. Thirty-seven of these modules are surface mounted to a large printed circuit board (PCB) 104 that is 380×760 mm. A common heat spreader 106 of similar dimensions is mated to the array of modules 102 and secured with several screws to fixed height standoffs (not shown). The voltage transformer module is sensitive to excessive mechanical compressive and tensile forces. In order to stay below these limited force levels, a very low modulus silicone gel TIM 108 was selected. This TIM easily accommodates the target nominal bond line of 1.5 mm, +/−0.5 mm. Separation forces were <0.03 MPa. The thermal resistance of 675 C mm$^2$/W at a nominal bond line was adequate for the application. There are other TIMs with lower thermal resistance (<350 C mm$^2$/W) that are still reworkable; however, the tensile separation forces exceeded the fragile limit allowed for the particular components employed in this embodiment. Initially, thermal pad TIMs were considered but, the compressive forces required to achieve the range of bond lines exceeded the fragile limit allowed for the component. The proposed capacitance technique could be used in applications where thermal pad TIMs are suitable for the particular component(s). It could also be used in applications where individual heat sinks are employed for each component, though greater benefit is likely obtained when used in assemblies including a heat spreader associated with multiple electronic components.

Studies and experiments were defined to measure and confirm that the bond lines met specifications, that the compressive and tensile forces did not exceed limits, and that the TIM remained in place during thermal and power cycling.

For non-electrically conducting TIMs, electrical capacitance between the component and the heat spreader can provide a direct probe of the bond line thickness and material integrity of the TIM. In this work, capacitance measurements were made of the thermal interface at all process stages, from initial squeeze out, to final bond line and during thermal mechanical stress testing. This technique provides a useful view of a critical part of the thermal path and exposes the effects of mechanical changes in the overall package that dramatically affect the TIM but can be nearly undetectable from outside the package.

Theory

Simplistically, the module and heat spreader with TIM in between is treated as a parallel plate capacitor. For a pair of parallel conductive plates of area, A, spaced a distance, g, apart, the capacitance, C, is given by:

$$C = \frac{\varepsilon_r \varepsilon_0 A}{g}, \qquad 1)$$

where $\varepsilon_0$=8.85e−12 Farads/meter is the permittivity of free space and $\varepsilon_r$ is the relative dielectric constant of the material between the plates. The inverse dependence on g makes capacitance a very useful and sensitive detector for gap measurements, especially at small gaps. Measuring the capacitance for parallel plates with a known spacing filled with the TIM material of interest allows one to determine its dielectric constant by solving equation 1. Subsequently, capacitance measurements can be made and used to calculate an average, effective bond line.

In certain circumstances, thermal conductance and capacitance have very similar geometrical and material property dependencies, making capacitance particularly relevant as an indicator of thermal performance. In uniform heat flow, the conductance, G, between parallel surfaces with a gap, g, filled with a material of conductivity k, and having an area, A, is given by:

$$G = \frac{kA}{g} \qquad 2)$$

Comparing equations 1 and 2, one can see that capacitance and thermal conductance both scale as area divided by gap, with dielectric constant playing the same role as material thermal conductivity.

In electronic assemblies, the component and heat spreader thermal conductivities are typically much higher than that of the TIM, but not infinite, so lateral gradients can be significant and the analogy to the electrical situation will be imperfect. Therefore, capacitance typically cannot be used as a substitute for detailed thermal modeling and measurement of packages. However, overall component to heat spreader capacitance does reflect the average thermal conductance of the TIM material and will track variations in thermal performance of parts. The measurement does not require special thermal test chips, so either early development, mechanically good hardware or standard production parts can be monitored. In addition, capacitance can be measured much more quickly and with higher precision than thermal resistance. This allows large numbers of parts to be studied, which reduces statistical uncertainty in design and process evaluation experiments. The theory behind the proposed capacitance technique is provided herein solely for explanatory purposes. The proposed technique has been found to be an effective tool regardless of theoretical assumptions.

EXPERIMENTAL

Several evolutionary experiments were completed that characterized the response of the design gap for the TIM at every step from initial heat spreader mating to the structural integrity of the TIM under cyclic, thermal mechanical strain. These experiments are described and discussed in three phases. Every phase provided insights that helped define the next set of experiments. Phase 1 used one assembly to quantify how the TIM gaps develop during heat spreader mating. Also, testing provided an early development look at how the TIM responded to cyclic, thermal mechanical strain induced during thermal cycling before thermal hardware was available. Phase 2 used ten (10) assemblies and compared TIM bond lines to design targets. The effectiveness of design changes that resulted from Phase 1 learning was studied in depth. In Phase 3 experiments, more realistic power cycling was performed and the impact of surfaces introduced as electrodes to make the capacitive bond line measurements was evaluated.

Phase 1 Experiments

Figure 19B:
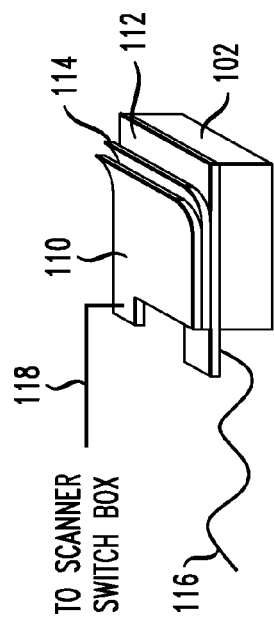
FIG. 19B is an enlarged perspective view of an electronic component and associated copper and dielectric layers.
Figure 20:
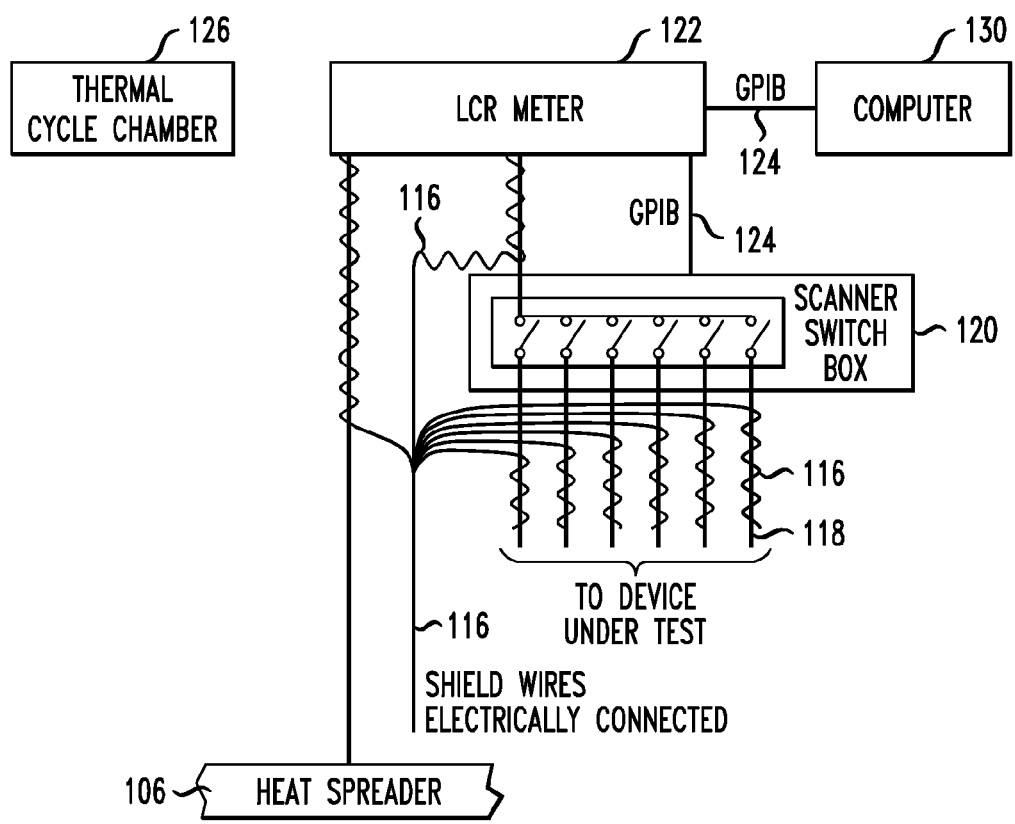
FIG. 20 is a schematic diagram showing an assembly for monitoring the capacitance of a plurality of electronic components in a device under test.

The first experiment was to determine how the bond line developed as a function of mating force, time and engagement of mechanical fasteners. Twenty of the thirty-seven components (modules) 102 were wired to make the capacitance measurement. A piece of copper tape with electrically insulating adhesive was applied to the entire surface of each of the twenty components, (The copper tape employed during the Phase 2 experiments discussed below included two copper layers 110,112 separated by a dielectric tape 114 as shown in FIGS. 19A and 19B.) The copper tape or layer adjoining the thermal interface material is used as an electrode of the capacitor. Wires 118 were soldered to areas of overhanging copper tape and carefully routed across the PCB surface, avoiding fastening standoffs and flow channel ribs in the heat spreader. The other ends of the wires were connected to a scanner switch box 120 that was connected to an LCR meter 122 set at 10 KHz and 1 volt drive. The second electrode was the heat spreader 106 and this was connected directly to the LCR meter. FIG. 20 provides an additional schematic illustration of the testing assembly showing further details of the scanner switch box 120 as well as the shielding 116 for the wires 118 added for the Phase 2 experiments. Six switches are shown for purposes of illustration in the scanner switch box, though more or less may be employed depending on the number of components 102 to be tested. As indicated above, twenty of the thirty-seven components were tested in the procedure and twenty switches were accordingly employed. Data acquisition was controlled by a personal computer 130 using BASIC programming and GPIB (General Purpose Interface Bus) 124. GPIB is one non-limiting example of suitable cabling; for example, USB (universal serial bus) or the like could be employed in other instances. After all the wiring and data logging connections were completed and the heat spreader was placed and secured, the parallel sum of stray and air gap capacitances was measured at each of the twenty test sites. There was stray capacitance from the voltage transformer module and PCB to the copper tape electrode on the module and from the heat spreader to the wires running from the copper tape electrode to the switch box. An average capacitance, $C_{ave}$, was determined for each site (40.00 to 65.00 pF, +/−0.03). Next, the heat spreader was removed, TIM 108 deposited and the heat spreader 106 was reattached. The sum of the parallel capacitances, stray and TIM, $C_2$, was measured. The stray capacitance was removed by subtracting the average air gap/stray capacitance from the measured TIM gap/stray capacitance. Assuming that the air and TIM gap are equal, the gap with the TIM 108 was calculated.

$$g_{TIM} = \frac{\varepsilon_0 A (\varepsilon_r - 1)}{C_2 - C_{ave}} \quad 3)$$

Capacitance, temperature and time were logged continuously. The mating force applied to the heat spreader was limited to 250 kg which was determined by assuming a uniform loading of all thirty-seven modules to 90% of the compressive limit. FIG. 1 is a plot of the TIM bond line vs. time and mechanical loading. The ultimate bond lines were not achieved with 250 kg mating force and time alone. Only after engaging the screws and securing to the standoffs were stable bond lines achieved, ranging between 1.2 to 1.7 mm.

Instantaneous loads can be very high when screws are engaged given the typical strain rate dependency of the TIM with respect to stiffness during compression. In order to ensure that the individual compressive loads on voltage converter modules were below the damage level, in-situ force measurements were made. A screw fastening sequence and rate were defined to keep the instantaneous loading on any single component in a safe region. The 250 kg loading was dropped from the heat spreader attachment process. Several of the bond lines were also measured by leaving out the TIM and placing a sandwich of room temperature curing epoxy between thin release layers, on the component surface. The heat spreader was placed when uncured epoxy was in place and it was removed after the epoxy cured. A precision micrometer was used to measure the cured disk of epoxy and the agreement with the bond line calculated from capacitance was within 10%. One difference in the two measurement methods was that the bond line calculated from capacitance represented the entire area of the component while the epoxy disks covered less than 10% of the area in the center.

Figure 2:
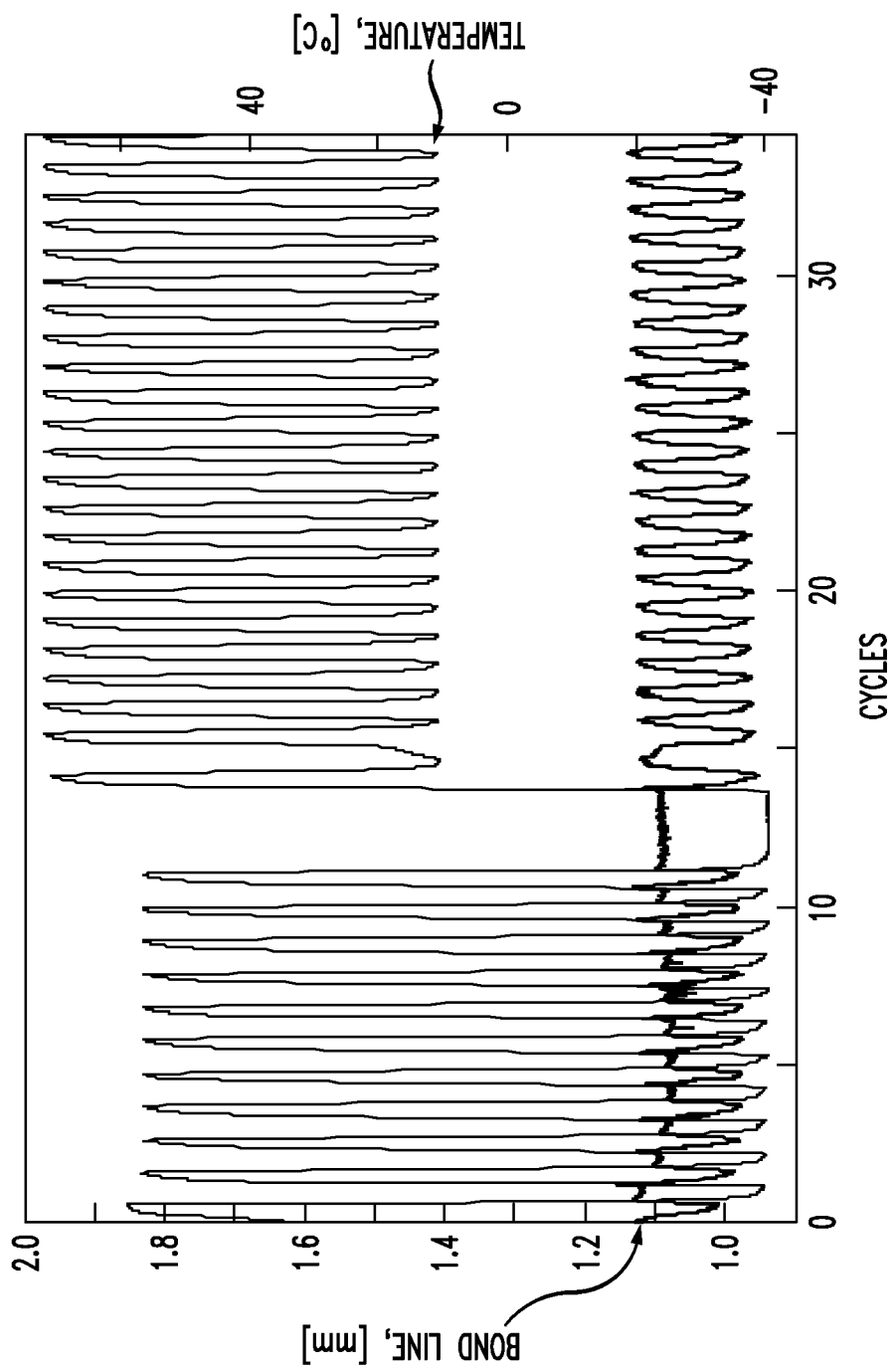
FIG. 2 shows a graph illustrating TIM bond line response to thermal cycling of a selected electronic assembly.

The next experiment was to monitor the integrity of the TIM in the assembly during thermal cycling. TIM was applied on the heat spreader to all thirty-seven component locations. After the heat spreader was mated and secured with screws, the capacitance was measured ten times on the bench to ensure that electrical connections were good and that the capacitance readings were stable, typically <0.01 pF. Next, the assembly was moved into a thermal cycle chamber 126 and the capacitance was measured ten times again. It is preferable to make sure the PCB assembly is always electrically isolated from earth or machine ground when the capacitance is being measured. If the heat spreader were connected to ground it may not be possible to measure the capacitance. The first ten thermal cycles were −40 C to 60° C. to represent the temperature extremes that are possible when shipping product. Under computer program control, capacitance readings were made on all twenty components every five minutes, continuously. After the ten shipping thermal cycles, the cycle was changed to 10 to 70° C., representing an over stress, power on/off cycle. FIG. 2 shows a typical bond line response vs. temperature cycling. During the cooling portion of the cycle, the bond line increases, indicating that there is a tensile force on the TIM. Conversely, during the heating portion of the cycle, the bond line decreases, indicating that there is a compressive force on the TIM. Total peak to valley TIM movement appears to be about 0.18 mm. However, it is believed that additional work would aid in quantifying the gap movement with greater certainty. The bond line calculation uses the dielectric constant of the TIM which could be changing during the thermal cycle. Air could be moving into or out of the bulk TIM and interfaces under the tensile and compressive loads during the thermal cycle. In a later experiment, gap motion is measured with no TIM present and the dielectric constant of air is used.

Figure 3:
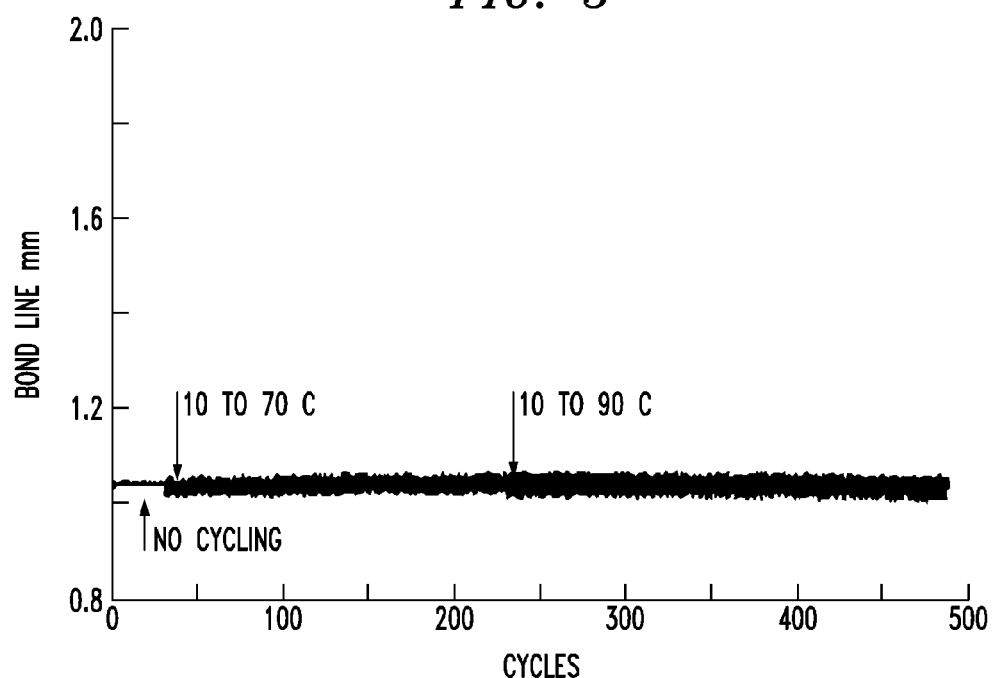
FIG. 3 shows a graph illustrating TIM bond line response of an electronic component in response to thermal cycling with peak to valley motion less than 0.05 mm.
Figure 4:
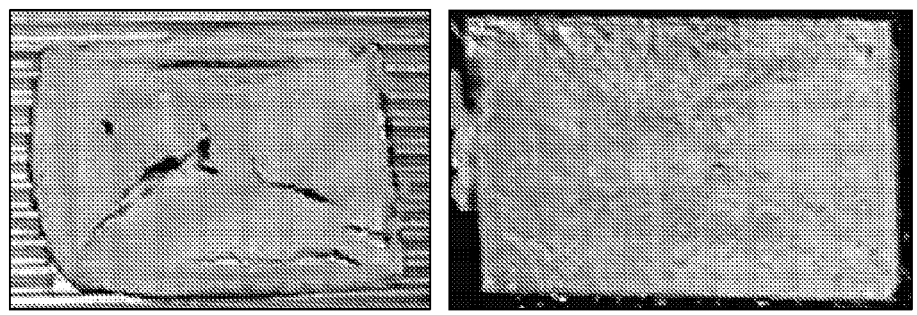
FIG. 4 shows photographs of residual TIM on a heat spreader location (left) and an electronic component (right) following thermal cycle testing.

The gap motion that is suggested by the 0.18 mm peak to valley estimate is a concern when compared to the results of tensile adhesion testing of individual components to individual heat spreader plates. These samples reached peaked tensile loads at about 0.22 mm elongation on a 1.5 mm bond line. For the twenty components that were measured, the range in peak to valley movement was <0.05 mm to almost 0.4 mm. FIG. 3 shows the results after almost 500 thermal cycles for a component that had a peak to valley change of <0.05 mm. The bond line is very stable and the amplitude of motion is not changing for a fixed thermal cycle. When the thermal cycle changes from 10-70° C. to 10-90° C., compression increases from 70 to 90° C. as shown in the plot in FIG. 3. FIG. 4 shows photos of the heat spreader site and the component after disassembly. The fissures that appear in the TIM on the heat spreader side are an indicator of structure weakness. Data taken from testing individual components mated to individual heat spreader plates (such individual plates representing, e.g., that portion of the common heat spreader that is immediately adjacent the component of interest) allows information characteristic of various physical conditions to be obtained. Such information can be helpful in identifying particular physical conditions, such as TIM degradation, that can be referenced when the individual component is associated with a heat spreader common to many components (for example, when monitoring an assembly in-situ during actual operation).

Figure 5:
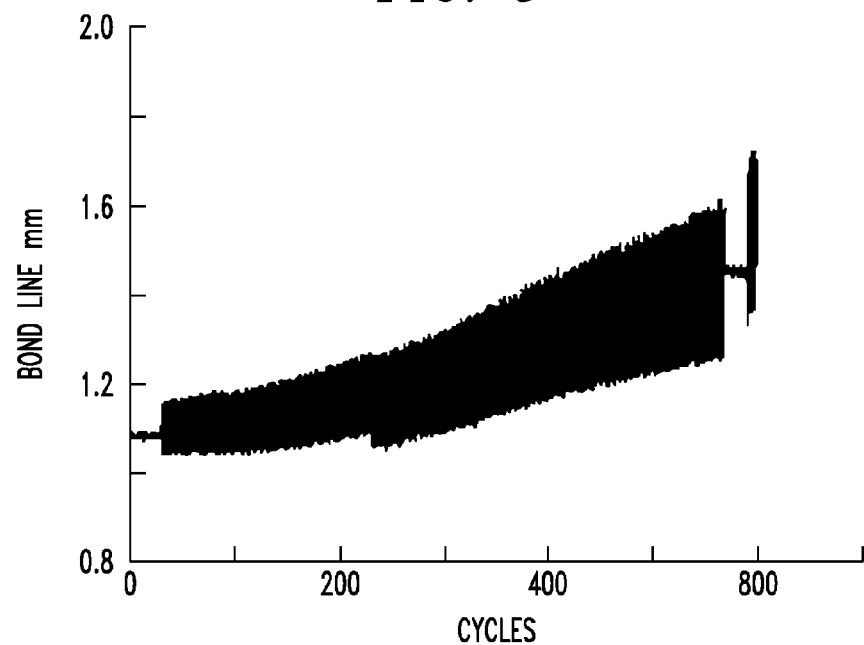
FIG. 5 shows a graph illustrating TIM bond line response of an electronic component in response to thermal cycling suggesting peak to valley motion of about 0.4 mm.

FIG. 5 shows the results of the capacitive bond line response for a component that had a peak to valley change of almost 0.4 mm. The bond line starts at about 1.1 mm and increases steadily during thermal cycle testing.

Figure 6:
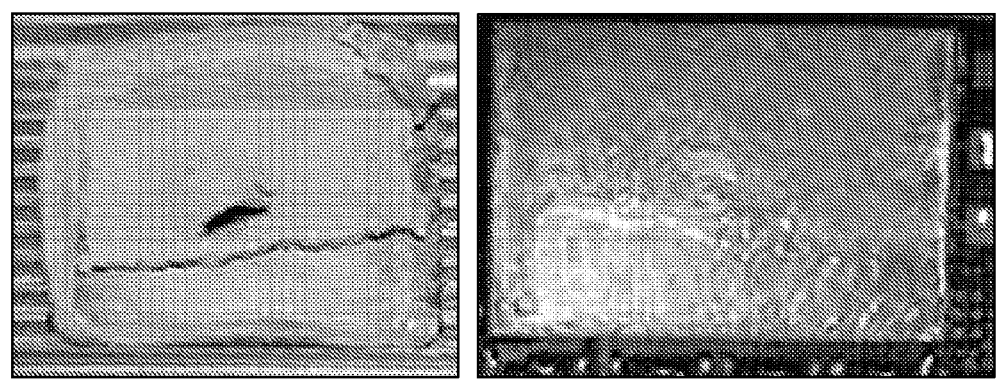
FIG. 6 shows photographs of a heat spreader location (left) and an electronic component (right) following thermal cycle testing and showing asymmetric fillets and about a 25% loss in TIM area.

A view of the photos in FIG. 6 helps explain the increasing trend in the FIG. 5 plot. It is obvious that the TIM is moving out of the gap from the thermal cycle induced motion. The capacitance is decreasing and would predict an increasing bond line. However, the decreasing capacitance is due to about a 25% loss of TIM area as shown in the lower portion of the heat spreader site. Note how the fillet at the top is much larger than the fillet at the bottom in the heat spreader site.

Only eight of the twenty sites (modules) that were monitored showed a stable capacitive bond line response throughout the thermal cycle testing. Ten sites showed an increasing capacitive bond line which equated to >15% loss of TIM area and asymmetrical fillets. The cause of the TIM movement is believed to be due to the cycles of compression during the heating portion of the cycle and tension during the cooling portion. Additional experiments were defined to quantify absolute motion, mitigate the TIM movement and compare thermal and power cycle induced motion.

Phase 2 Experiments

In order to achieve higher accuracy in measuring absolute gap movement without the TIM present, two improvements to the Phase 1 experiments were made that reduced the stray capacitance an order of magnitude (from 40 to 4 pF). The improvements are shown in FIGS. 19A, 19B and FIG. 20. Instead of using unshielded wire which picked up stray capacitance from the heat spreader 106, coaxial cable was used. The outer conductor 116 was an electrical shield that blocked the stray capacitance from the heat spreader 106 to the inner conductor 118 which was used to make the capacitance measurement. In addition, the copper tape was comprised of two layers separated by a dielectric material. The first layer 112 of copper tape on the components 102 was connected to electrical shield 116 and blocked capacitive coupling from the component and PCB 104. The second layer 110 of copper tape was placed over the shield layer 112 and was connected to the inner conductor 118 of the coax wire which was connected to a scanner channel. The dielectric, layer 114 helps prevent electrical shorting between the two copper layers. All the shield wires were electrically interconnected near the scanner switch box and connected to the shield of the LCR meter 122. The stability of the stray capacitance vs. temperature was measured to be <0.04 pF in the worst case.

Figure 7:
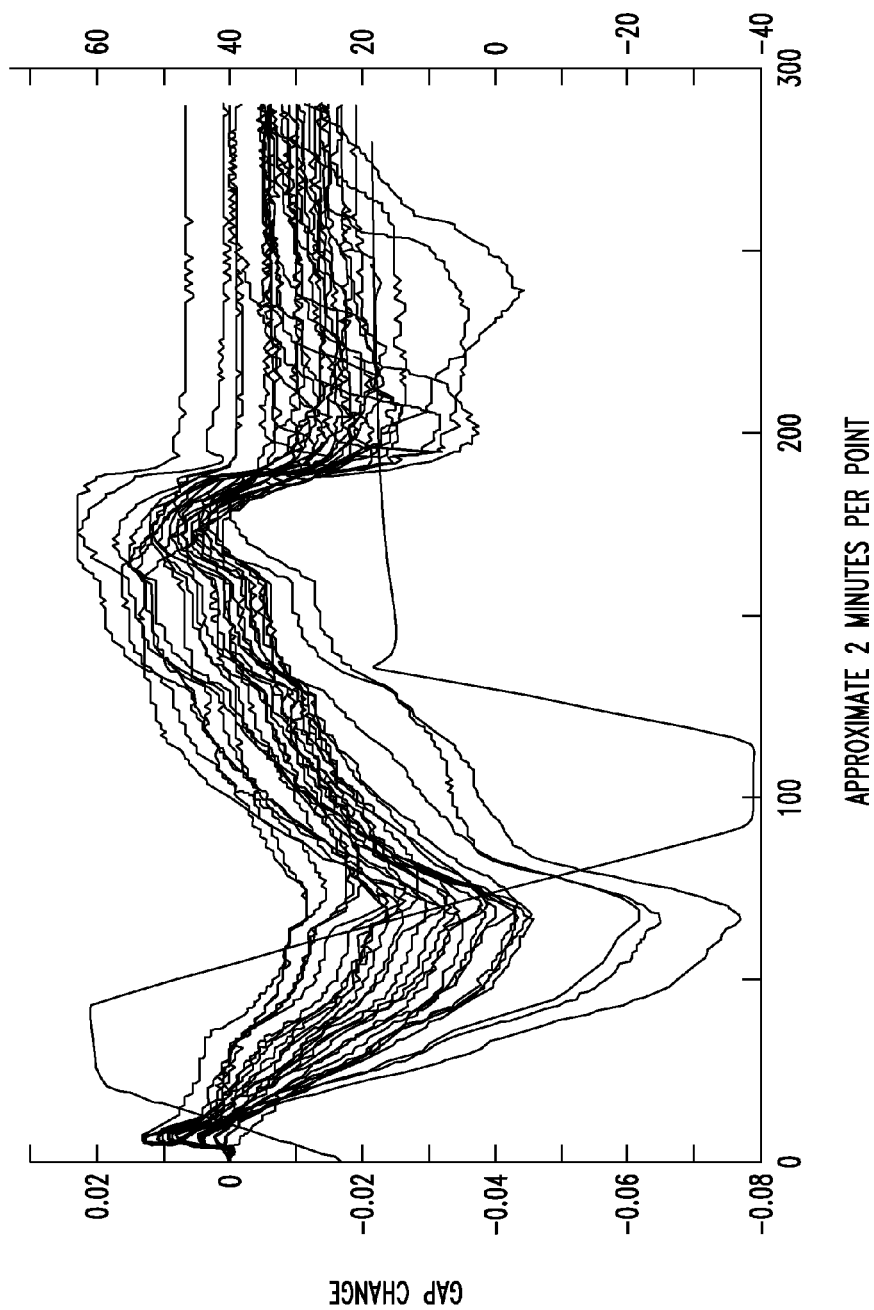
FIG. 7 shows a graph illustrating absolute air gap motion for a plurality of electronic components during a thermal cycle from −40 to 60° C.
Figure 8:
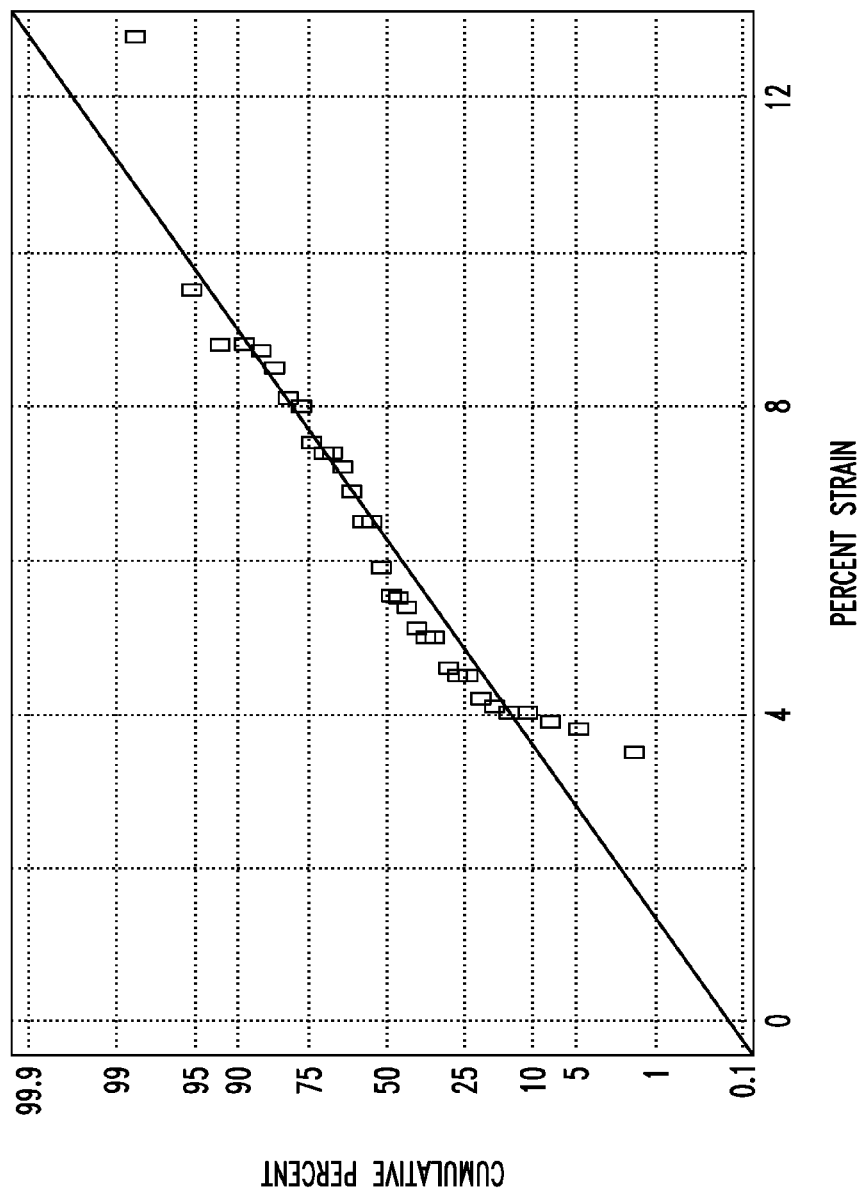
FIG. 8 shows a graph illustrating distribution of strain in air gaps for thirty-two electronic components.

FIG. 7 shows the air gap changes for all components during a ship shock thermal cycle between −40 C and 60 C. Consistent with the trend in the first test, at the cold temperature, the air gap increases as much as twenty (20) microns, and at the hot temperature, it decreases as much as eighty (80) microns. The air gap motion was converted to strain for correlation to changes in capacitive bond line of the TIM during thermal cycling and evidence of pumping. The nominal air gap strain was six percent, as seen in FIG. 8.

Quantifying the gap motion enabled studies on how to reduce or eliminate TIM movement. Roughening the heat spreader surface has been found to reduce thermal-cycling-induced movement of thermal greases. Strain controlled, cyclic testing was completed on individual components mated to heat spreader surfaces. Heat spreaders were prepared with N8 and N9 surface finishes. (N8 is believed to correspond to an average surface roughness of 3.2 microns while N9 is believed to correspond to an average roughness of 6.3 microns.) Air gap measurements were made during a thermal cycle between −40 and 60° C. The heat spreader was removed, TIM was deposited onto the surfaces where the components mated and it was reattached. Ten cycles of −40 to 60° C. were followed by 350 thermal cycles from 10 to 70° C. As before, stray capacitance was measured for every component before the TIM was deposited so that it could be subtracted from the capacitance measured with the TIM present. Capacitance measurements were made every five minutes on thirty-two components (modules).

Figure 9:
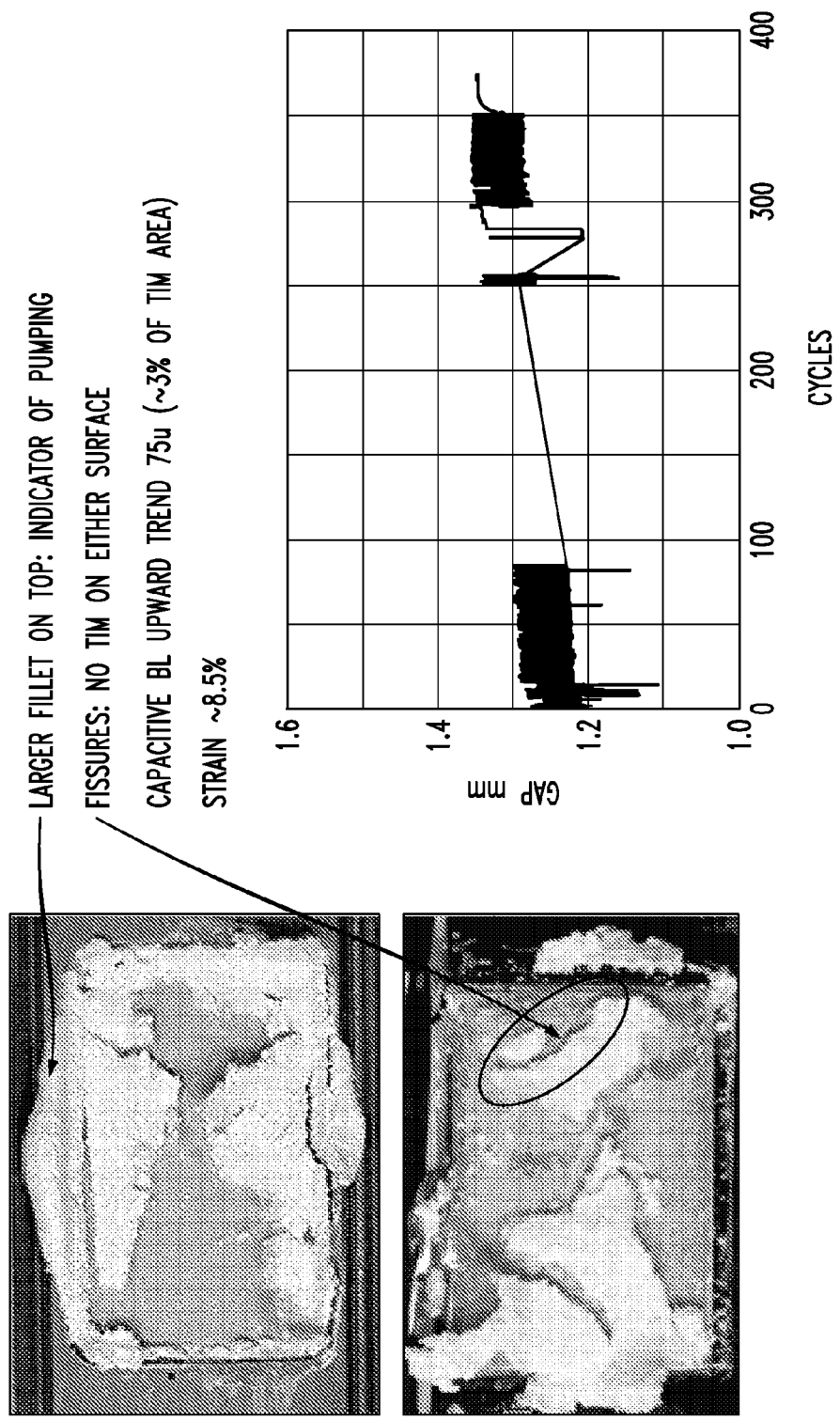
FIG. 9 shows photographs of a heat spreader location (top left), an electronic component (bottom left) following a thermal cycle test, and a graph illustrating the gap between the electronic component and the heat spreader as a function of thermal cycles.

FIG. 9 shows the results for a high strain (8.5%) component site. The capacitive bond line shows an upward trend suggesting some TIM pumping. The photos provide evidence of TIM pumping showing asymmetric fillets and fissures in the TIM. The decrease in capacitance equates to a three percent loss in area.

Figure 10:
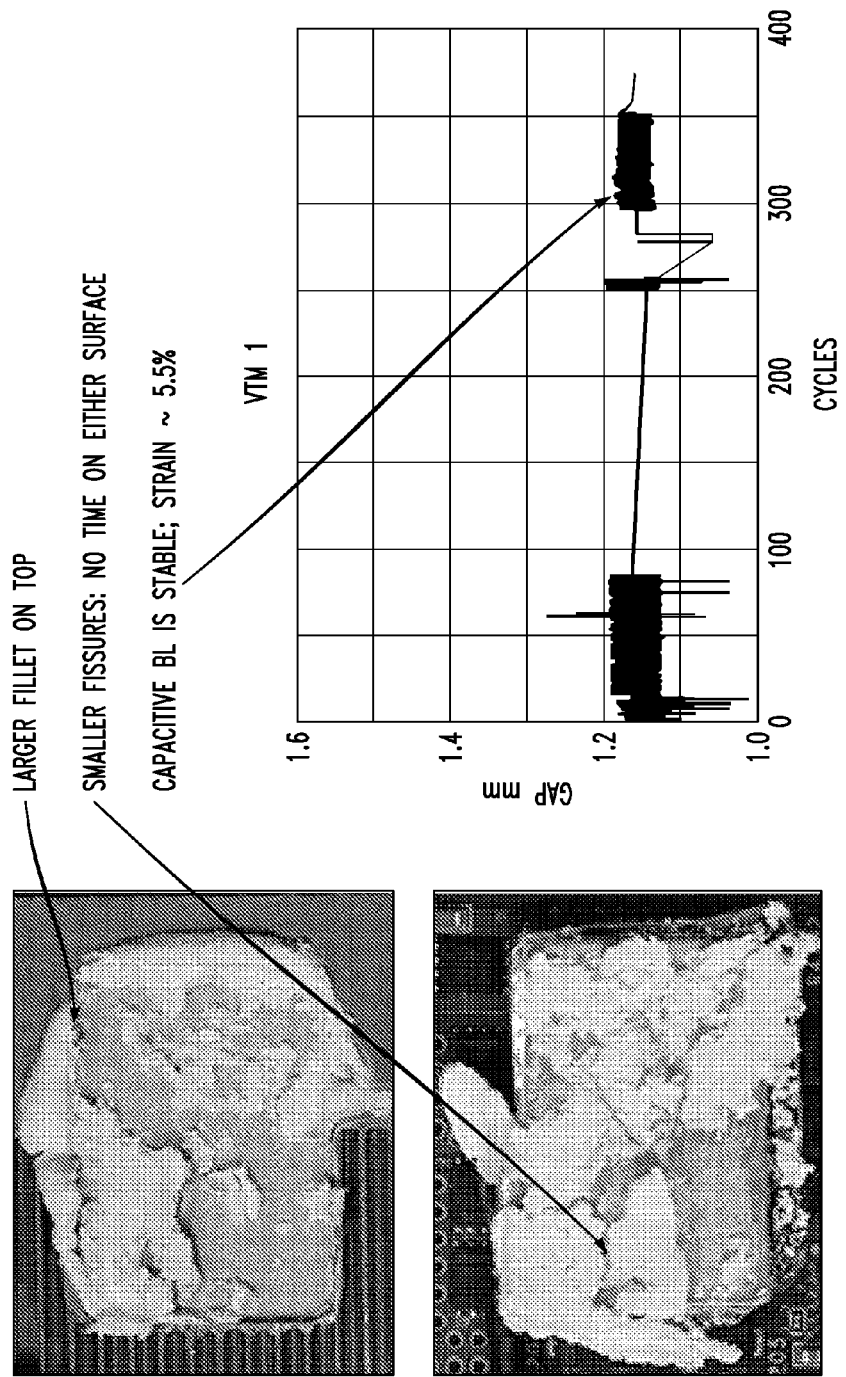
FIG. 10 shows photographs of a heat spreader location (top left) and an electronic component (bottom left) following a thermal cycle test, and a graph illustrating the gap between the electronic component and a heat spreader as a function of thermal cycles.

FIG. 10 shows the results for a nominal strain (5.5%) component site. The capacitive bond line is stable suggesting no significant TIM pumping. The precursors to TIM pumping, asymmetric fillets and fissures in the TIM are evident in the photos in FIG. 9.

Figure 11:
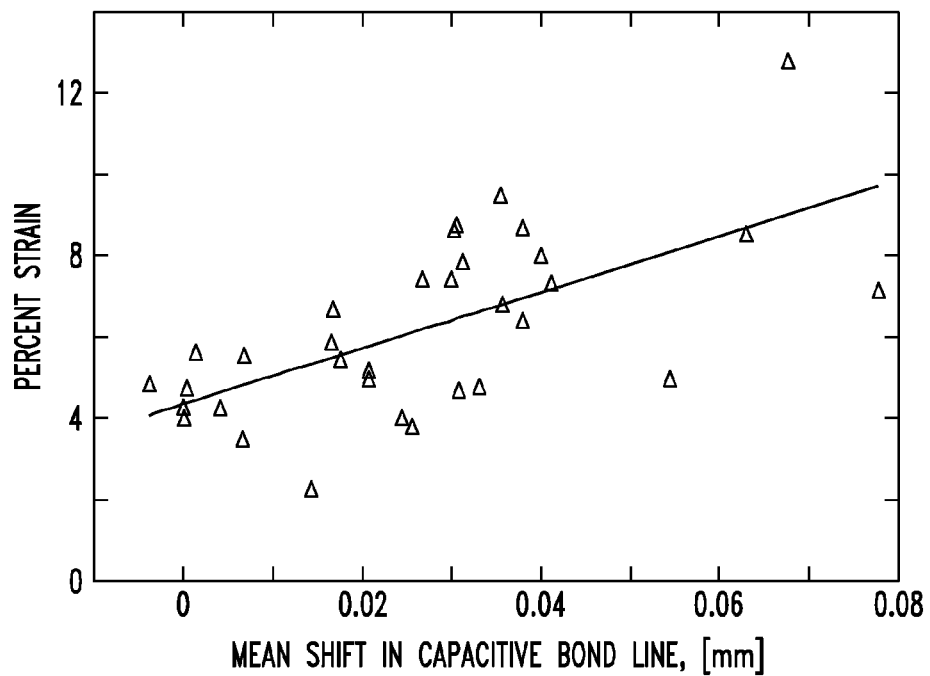
FIG. 11 shows a graph illustrating correlation between strain and mean shift in capacitive bond line.

The plot in FIG. 11 shows that there is a mild correlation between the air gap strain and the mean shift in capacitive bond line for the thirty-two components that were tested.

The results for the roughened heat spreader were an improvement compared to the first test with the non-roughened heat spreader. However, the evidence that there was still a low level of TIM pumping directed further study. One objective was to determine if the copper tape electrodes 110 caused a different response compared to a component 102 without the electrodes. Another objective was to compare thermal cycling to more realistic power cycling.

Phase 3 Experiments

Figure 12:
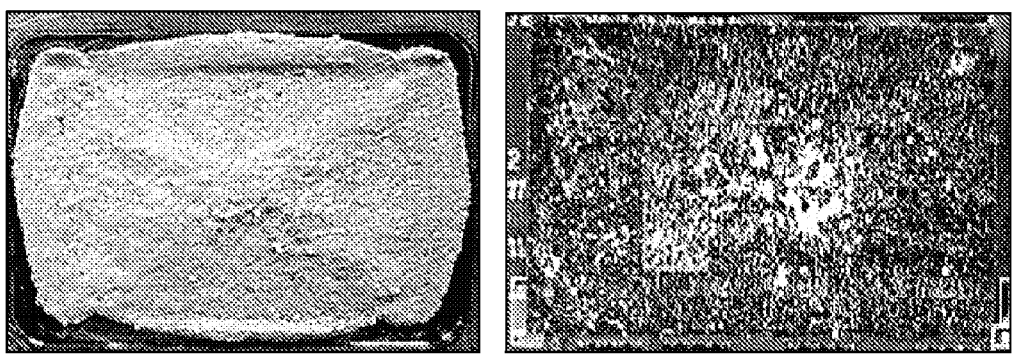
FIG. 12 shows photographs of a smooth heat spreader location (left) and the bottom of an electronic component (right) after power cycle testing and not showing evidence of TIM pumping.
Figure 13:
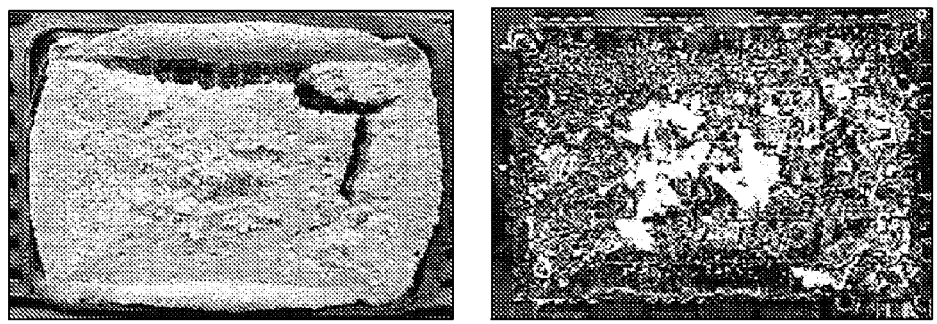
FIG. 13 shows photographs of a smooth heat spreader location (left) and the bottom of an electronic component (right) after power cycle testing and showing evidence of TIM pumping.
Figure 14:
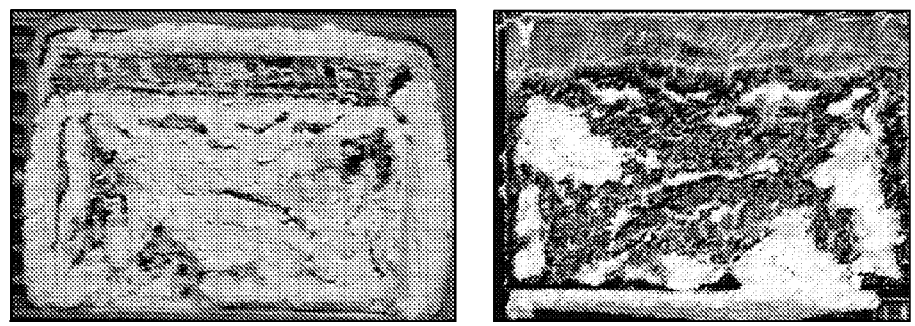
FIG. 14 shows photographs of a smooth heat spreader location (left) and an electronic component (right) after thermal cycle testing without using a copper electrode, the photographs showing evidence of TIM pumping including about a twenty percent loss in TIM area.

The disassembly results after phases 1 and 2 showed the presence of the precursors to pumping and TIM pumping. These results were used to help interpret the TIM responses when no copper tape electrodes were present during both thermal and power cycling. First, a heat spreader without roughening (smooth) was used and, using a power source 128 as shown in FIG. 19A, approximately 500 system power up and down cycles were run. During disassembly, it was observed that ten (10) out of thirty-seven (37) components 102 showed no evidence of TIM pumping as represented in FIG. 12. However, the other twenty-seven components had evidence of TIM pumping: asymmetric fillets (8), fissures (15), both asymmetric fillets and fissures (4) and 5-15% loss of TIM area (10). FIG. 13 shows a typical response with an asymmetrical fillet and a large fissure that represents a loss in TIM area of about 10%. The same node assembly was prepared for thermal cycle testing out to 350 cycles. Similar TIM movement occurred in both power cycling (FIG. 13) and thermal cycling (FIG. 14) when a smooth heat spreader was used and no copper tape electrodes were present.

Figure 15:
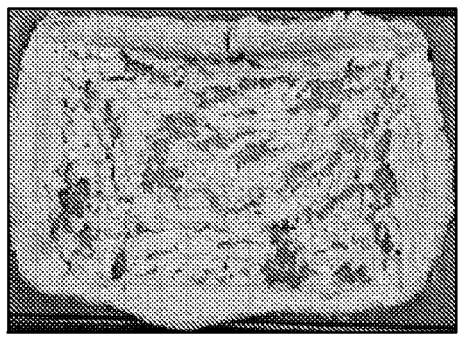
FIG. 15 shows photographs of a heat spreader location (left) and an electronic component after a thermal cycle test without using a copper electrode and wherein the heat spreader has a surface roughened to N9, no evidence of TIM pumping being present.
Figure 15:
Figure 16:
FIG. 16 shows photographs of a heat spreader location (left) and an electronic component (right) after power cycle testing without using a copper electrode, the heat spreader having a surface roughened to N9, no evidence of TIM pumping being present.
Figure 16:
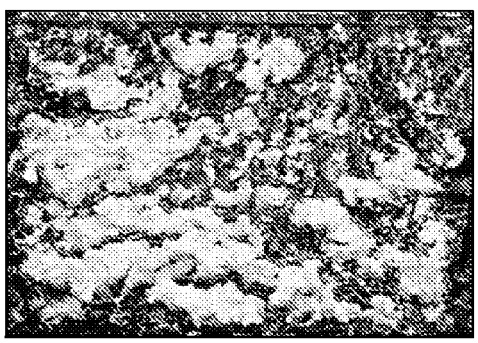

Next, the response for a heat spreader with an N9 surface finish was compared after exposure to 1250 power cycles and more than 1000 thermal cycles, again without any copper tape electrodes. FIGS. 15 and 16 are photos of typical sites after thermal and power cycling, respectively. In these figures, there is no significant evidence of TIM pumping. On other components not shown, there are infrequent occurrences of very small fissures that do not add up to any quantifiable loss in TIM area.

It is concluded that the copper electrodes on the components do not alter the results of TIM pumping for the smooth heat spreaders. The benefit of roughening the heat spreader is also evident when the copper electrodes are used. However, the precursor evidence to TIM pumping is nearly completely absent on the assembly that was thermal cycled without copper tape electrodes on the components. In contrast, twenty-seven (27) out of thirty-seven (37) components with copper tape electrodes that were thermal cycled showed the precursor signs of TIM pumping. In this test, though, the capacitive bond line was stable on all components.

Figure 17:
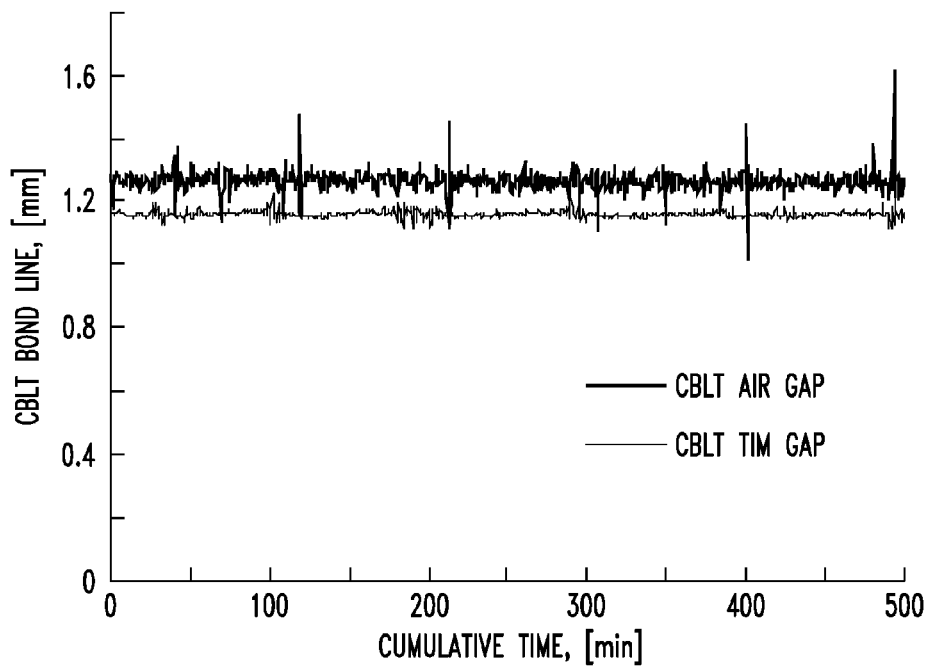
FIG. 17 shows a graph indicating capacitive gap measurements during power cycling, the gap being with and without TIM.

One last test was performed to quantify the gap motion during power cycle and compared to the range of 100 microns that was previously measured in thermal cycle. Power cycling was performed with and without TIM. The agreement in the absolute gap measurements that were made with and without TIM was 12% or less, as shown in FIG. 17. As seen therein, capacitive gap measurements during power cycling are consistent with and without TIM.

Figure 18:
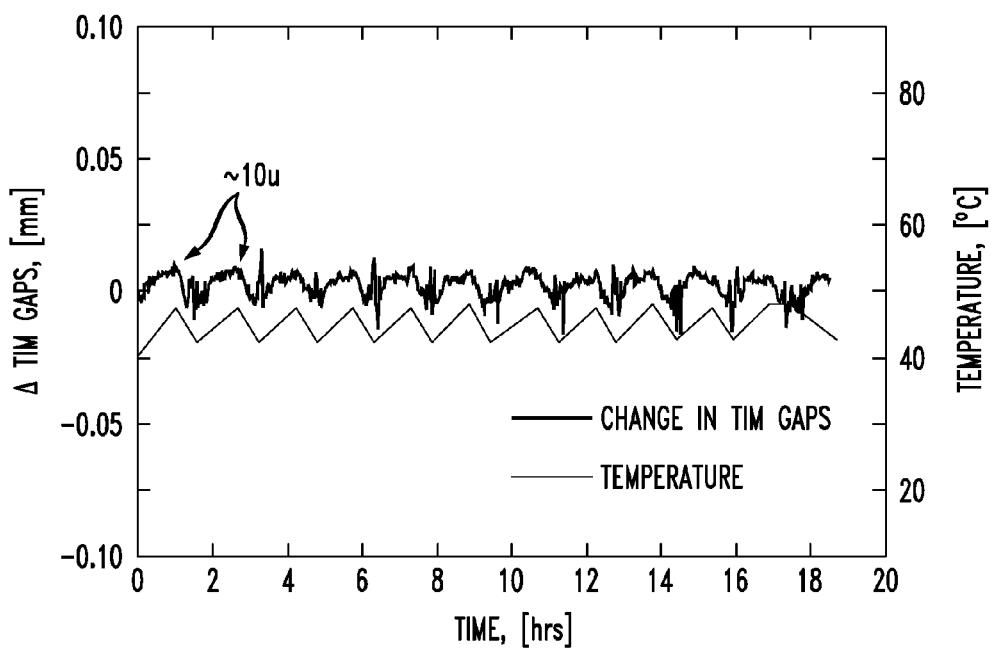
FIG. 18 shows a graph illustrating TIM gap motion during power and temperature cycling.

The measurements were less noisy for the TIM gaps compared to the air gaps because of the 3.45 dielectric constant of the TIM. Consequently, changes in gap during power cycling were quantified using the TIM. The range in motion was only 10 microns compared to 100 microns that was measured in thermal cycling, as shown in FIG. 18.

Findings based on use of the capacitance measurements as discussed above include:

1. Assemblies with a smooth heat spreader experience increasing capacitive bond line during thermal cycle testing equivalent as much as 25% of area loss in TIM. TIM pumping occurs with and without copper tape electrodes during thermal cycling and without copper electrodes during power cycling. (Extended power cycling was not done with copper electrodes on the component surfaces.)
2. Assemblies with an N9 heat spreader and copper tape electrodes have a more stable capacitive bond line and equivalent area losses in TIM are less than 5%. Precursors to TIM pumping are evident: fissures and asymmetric fillets
3. Assemblies with an N9 heat spreader but without copper tape electrodes have very few and small fissures after both thermal and power cycling. No quantifiable area loss in TIM is observed.
4. The range of motion in power cycling is a factor of (10) less than in thermal cycling.

The combined benefits of a roughened heat spreader surface and an order magnitude less gap motion in power cycling compared to thermal cycling provide confidence that thermal performance will be maintained under operational life.

Monitoring the response of the TIM with capacitance is easy and provides timely insight throughout the development cycle. Confidence can be gained on the reliability of the thermal solution well before thermal hardware is available for final system level thermal testing.

Figure 19C:
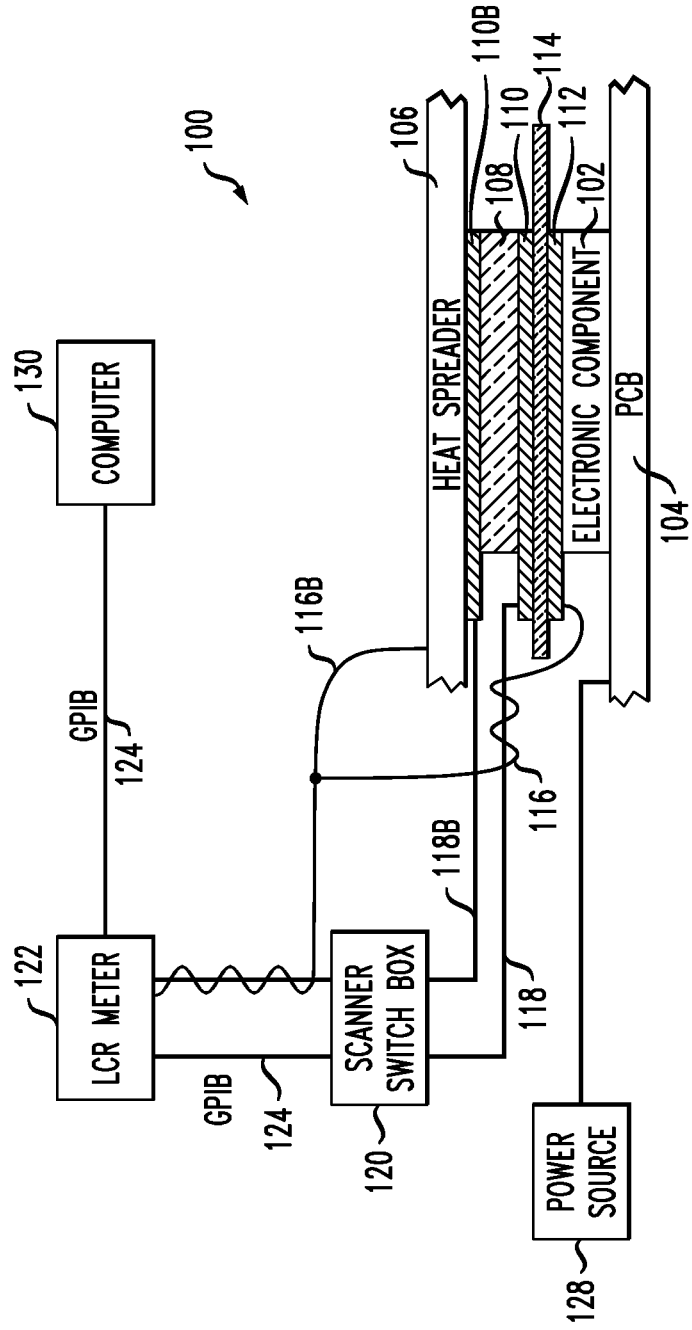
FIG. 19C is a schematic diagram showing the assembly of FIG. 19A wherein the heat spreader is configured to function as an electrical shield.

FIG. 19C shows a modified assembly similar to that shown in FIG. 19A. The same reference numerals found in FIG. 19A are employed in FIG. 19C to designate similar elements. In this assembly, the heat spreader 106 additionally functions as an electrical shield to reduce the electrical noise during system power-on. The heat spreader 106 is electrically connected to a shield connection 116B. The shield connection 116B is electrically coupled to the electrical shield 116. A layer of copper tape 110B is applied to the heat spreader and matched to the component location and area. The copper tape 110B is connected to the scanner switch box 120 and is electrically isolated from the heat spreader by a thin layer of dielectric material (not shown). The copper tape 110E accordingly functions as one of the parallel plates of a capacitor, the second plate comprising the copper layer 110. The heat spreader 106, being electrically isolated from the system and earth ground, acts as an electrical shield and blocks out capacitive coupling from the electrically active system.

Figure 21:
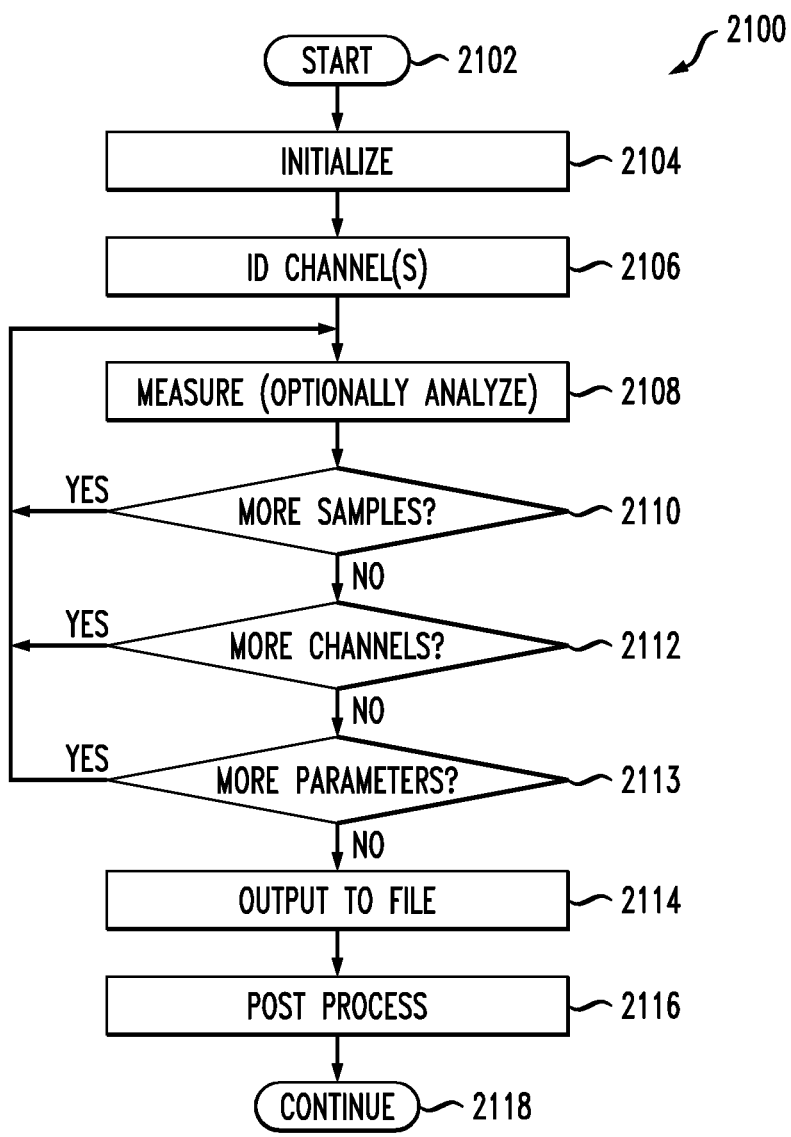
FIG. 21 is a flow chart of exemplary method steps, according to an aspect of the invention.

FIG. 21 presents a flow chart 2100 of exemplary method steps, according to an aspect of the invention. Processing begins at 2102. In step 2104, appropriate initialization is carried out; for example, initialize the LCR meter under GPIB or similar control (also initialize the scanner in one or more embodiments). The meter should be set to the desired test mode (e.g., capacitance as opposed to inductance or resistance) and the drive voltage, frequency, and time between measurements (e.g., 10 seconds, 30 seconds, 50 seconds, or other appropriate value) should be set. Of course, in other instances, a capacitance only meter could be used. In step 2106, identify the channel(s) to be measured in this instance for the particular device(s) under test (DUT) (for example, consult a look-up table). Beginning at a suitable channel (e.g., channel 1), select the required channel on the scanner switch and begin making one or more measurements for that channel, in step 2108. As shown at decision block 2110, in a typical case, multiple measurements are made on each channel and the mean and standard deviation are determined. A clip level can be set to reject extraneous data, if desired. Where more readings on the same channel are required ("Y" branch of block 2110), loop back to 2108. Where no more readings on the same channel are required ("N" branch of block 2110), proceed to decision block 2112 and determine if there are more channels to be tested. If so ("Y" branch of 2112), loop back to 2108 and test for those channels. If not ("N" branch of 2112), proceed to 2113. In step 2113, the pertinent environmental parameters or other boundary conditions can be varied (deliberately or as may occur in-situ during use); if more variations are to be tested, return to step 2108 as per the "Y" branch; else, proceed to step 2114 and output a suitable data file including measurements (capacitance), channel, time when taken, and optionally, pertinent environmental parameters or other boundary conditions such as temperature, humidity, power dissipated, applied assembly force or pressure, vibration input, and the like.

In step 2116, carry out post processing on the data file to determine the presence of signatures of anomalies such as TIM pumping or other bond line degradation. This step can include converting capacitance to the parameters of interest, such as bond line thickness, thermal conductance, or the like. For example, measure the capacitance of the DUT, subtract out the stray capacitance, and determine g from equation (1). With reference to FIG. 5 (bond line increasing with cycle), exemplary information of interest might include the amplitude of bond line change with temperature, amplitude of total excursion of bond line over a number of cycles (flat slope desirable but increasing slope undesirable).

Processing continues at 2118.

As noted at 2108, in addition to or in lieu of post-processing step 2116, real time examination for anomalies such as TIM pumping or other bond line degradation can be carried out at any suitable point during the data gathering process (within step 2108 being but one non-limiting example).

Given the discussion thus far, it will be appreciated that, in general terms, an exemplary method for monitoring thermal interface material in the gap between an electronic component and a heat spreader, according to an aspect of the invention, includes the step of applying an electric potential to first and second electrodes on opposite sides of the gap. At least one of the thermal interface material, electronic component and heat spreader is subjected to a changing physical condition such as pressure, temperature cycling and/or power cycling. The electrical capacitance between the electrodes is monitored during the changing physical condition. The method can be applied to a plurality of electronic components that are mounted to a PCB and use a common heat spreader.

The principles of the invention may be applied to monitoring various interfaces between elements, including interfaces comprising bond lines made of materials having dielectric properties such as thermal interface materials as discussed above, adhesives, and other dielectric materials positioned between two elements. One or more of the elements may be an electronic component such as a module or microprocessor. Alternatively, it may be useful to monitor interfaces outside the field of electronics. The capacitance between electrodes strategically positioned at such interfaces can be monitored by equipment as disclosed herein, in situ and in real time, providing information relating to the interfaces and the material, if any, positioned within the interfaces. In this manner it may be possible to monitor for possible degradation at interfaces of load-bearing structures or other structures where changes at interfaces are useful to know but may otherwise be difficult to determine visually or by other means. Non-limiting examples include adhesive bonds in a variety of contexts, such as automotive, aerospace, and construction and civil engineering applications (including initial assembly integrity and in-situ monitoring over time).

Furthermore, given the discussion thus far, it will be appreciated that, in general terms, an exemplary assembly for testing thermal interfaces, according to an aspect of the invention, includes a PCB, a plurality of electronic components mounted to the PCB, heat spreader, a first electrode associated with the heat spreader, a plurality of second electrodes associated, respectively, with the electronic components, and a device for monitoring the capacitances between the first and second electrodes. The heat spreader preferably comprises the first electrode. Thermal interface material may be positioned between the first and second electrodes.

The principles of the invention can be applied to constructing an assembly for either testing or long term purposes. An example of a construction method that allows external monitoring of a completed assembly includes providing a plurality of components, thermal interface materials, electrode plates and conductors, and assembling these elements to form an integral structure wherein a plurality of interfaces are provided between components, the electrode plates are positioned within the interfaces, the interface material is positioned between the electrodes, and the conductors are electrically connected to the electrode plates and externally accessible on the integral structure. The method may further include connecting an apparatus for measuring electrical capacitance and connecting the apparatus to the conductors. The apparatus does not necessarily need to cause the display of units of electrical capacitance as it may be sufficient only to know that the electrical capacitance between electrode plates has changed or that the electrical capacitance measured between one set of electrode plates is materially different from one or more other sets of plates. Electrode plates can be incorporated within the integral structure at locations that may be deemed critical, most subject to failure, most difficult or impossible to visually inspect, and/or at random. The integral structure constructed in this manner can be monitored at the site of the structure or at a remote site. The interfaces can be monitored simultaneously or individually.

Thus, aspects of the invention include a test method, a method of designing a thermal interface based on such testing, a computer program product which facilitates such testing, a test set-up or apparatus, a method of construction, and a test assembly wherein the components to be tested are mounted in connection with the test set-up or apparatus.

Exemplary System and Article of Manufacture Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

Figure 22:
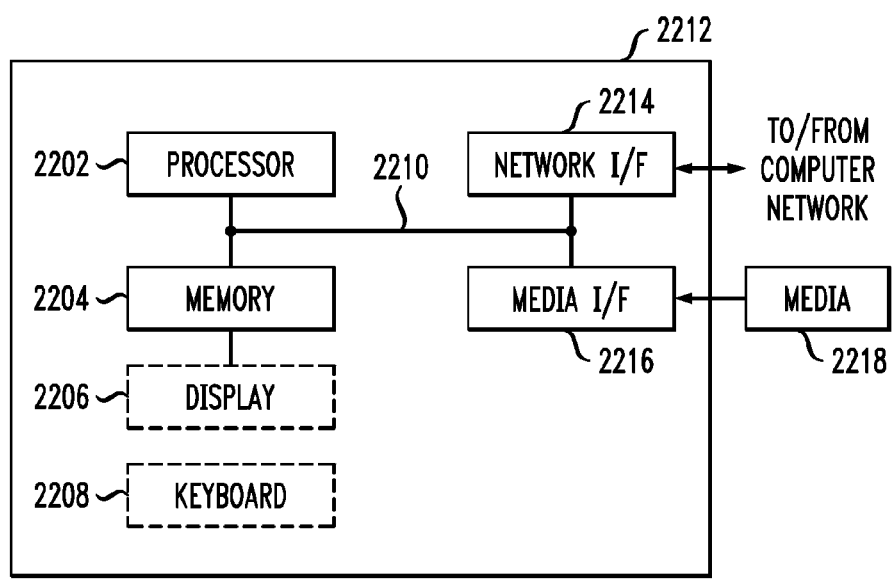
FIG. 22 depicts a computer system that may be useful in implementing one or more aspects and/or elements of the invention.

One or more embodiments can make use of software running on a general purpose computer or workstation. With reference to FIG. 22, such an implementation might employ, for example, a processor 2202, a memory 2204, and an input/output interface formed, for example, by a display 2206 and a keyboard 2208. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the phrase "input/output interface" as used herein, is intended to include, for example, one or more mechanisms for inputting data to the processing unit (for example, mouse), and one or more mechanisms for providing results associated with the processing unit or example, printer). The processor 2202, memory 2204, and input/output interface such as display 2206 and keyboard 2208 can be interconnected, for example, via bus 2210 as part of a data processing unit 2212. Suitable interconnections, for example via bus 2210, can also be provided to a network interface 2214, such as a network card, which can be provided to interface with a computer network, and to a media interface 2216, such as a diskette or CD-ROM drive, which can be provided to interface with media 2218.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 2202 coupled directly or indirectly to memory elements 2204 through a system bus 2210. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 2208, displays 2206, pointing devices, and the like) can be coupled to the system either directly (such as via bus 2210) or through intervening I/O controllers (omitted for clarity).

Network adapters such as network interface 2214 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 2212 as shown in FIG. 22) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 2218 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, ding an object oriented programming language such as Java, Smalltalk, C++ or the like and conventional procedural programming languages, such as the "C" programming language, BASIC programming language, or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet. Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein; by way of example and not limitation, an initialization module, a module to cycle through the test points and parameters, an output module to generate the output file, a post-processing module to reduce the data and search for anomalies, and the like. The method steps can then be carried out using the distinct software modules and/or sub-modules of the system, as described above, executing on one or more hardware processors 2202. Further, a computer program product can include a computer-readable storage medium with code adapted to be implemented to carry out one or more method steps described herein, including the provision of the system with the distinct software modules.

In some instances, changing the external temperature induces motion when components have different coefficients of thermal expansion; in addition or as an alternative, a mechanical force can be applied to the heat spreader, to cause a local deformation, and the capacitance response can be monitored close to the point of mechanical perturbation. The aforementioned module to cycle through the test points and parameters could be used to control changes in temperature and/or force application.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for monitoring the response of thermal interface material located in a gap between an electronic component and a heat spreader, comprising:

providing a tape including a first layer of electrically conductive tape within the gap and above the electronic component, a second layer of electrically conductive tape within the gap and between the first layer of electrically conductive tape and the thermal interface material, and a dielectric layer between and electrically isolating the first and second layers of electrically conductive tape, the second layer of electrically conductive tape comprising a first electrode;

applying an electric potential to the first electrode and to a second electrode on an opposite side of the thermal interface material, the first layer of electrically conductive tape blocking capacitive coupling from the electronic component;

subjecting at least one of the thermal interface material, the electronic component and the heat spreader to a changing physical condition;

monitoring changes in the electrical capacitance between the electrodes during and caused by the changing physical condition, and outputting data reflecting changes in the monitored electrical capacitance during the changing physical condition.

2. The method of claim 1, wherein the changing physical condition comprises pressure applied to the heat spreader in the direction of the electrical component.

3. The method of claim 1, wherein the changing physical condition comprises temperature cycling.

4. The method of claim 1, wherein the changing physical condition comprises power cycling of the electronic component.

5. The method of claim 1, further comprising electronically converting monitored electrical capacitance to a selected physical parameter.

6. The method of claim 1, further comprising providing a printed circuit board having a plurality of electronic components mounted thereto, the heat spreader and the plurality of electrical components defining a plurality of gaps, the thermal interface material being present in the gaps, wherein the method further comprises monitoring the electrical capacitance between electrodes on opposite sides of the gaps.

7. The method of claim 6, wherein the heat spreader comprises the first electrode.

8. The method of claim 6, wherein the changing physical condition comprises pressure applied to the heat spreader in the direction of the electronic components.

9. The method of claim 6, wherein the changing physical condition comprises temperature cycling.

10. The method of claim 6, wherein the changing physical condition comprises power cycling of the electronic components.

11. A computer program product for monitoring the response of thermal interface material located in a gap between an electronic component and a heat spreader, said computer program product comprising:
　　a non-transitory computer readable storage medium having computer readable program code embodied therewith for causing a computer processor to:
　　facilitate applying an electric potential to first and second electrodes on opposite sides of the gap;
　　while at least one of the thermal interface material, the electronic component and the heat spreader is subject to a changing physical condition, monitor the electrical capacitance between the electrodes during the changing physical condition
　　control said changing physical condition during a test procedure, and
　　facilitate an output of data reflecting changes in the monitored electrical capacitance during and caused by the changing physical condition.

12. The computer program product of claim 11, further comprising computer readable program code configured to convert monitored electrical capacitance to a selected physical parameter.

13. The computer program product of claim 11, wherein the changing physical condition comprises power cycling of the electronic component.

14. The computer program product of claim 11, wherein the changing physical condition comprises temperature cycling.

15. The computer program product of claim 11, wherein the changing physical condition comprises pressure applied to the heat spreader in the direction of the electrical component.

\* \* \* \* \*